United States Patent

Volkwein et al.

[11] 4,355,189
[45] Oct. 19, 1982

[54] PROCESS FOR THE PREPARATION OF 4-PHENOXYPHENOLS

[75] Inventors: Gert Volkwein, Kelkheim; Hubert Schönowsky, Rödermark; Konrad Baessler, Frankfurt am Main, all of Fed. Rep. of Germany

[73] Assignee: Hoechst Aktiengesellschaft, Frankfurt am Main, Fed. Rep. of Germany

[21] Appl. No.: 232,210

[22] Filed: Feb. 6, 1981

[30] Foreign Application Priority Data

Feb. 8, 1980 [DE] Fed. Rep. of Germany ....... 3004610

[51] Int. Cl.$^3$ ............................................. C07C 41/26
[52] U.S. Cl. ................................... 568/637; 568/638; 260/208
[58] Field of Search ....................... 568/637, 638, 767; 260/208

[56] References Cited

FOREIGN PATENT DOCUMENTS

| 2648644 | 5/1978 | Fed. Rep. of Germany ...... 568/637 |
| 1038185 | 8/1966 | United Kingdom ................ 568/637 |
| 391128  | 4/1973 | U.S.S.R. ............................... 568/638 |

OTHER PUBLICATIONS

Hilgetag, Weygand/Hilgetag, Preparative Organic Chemistry, (1972), 581–583, 342–345.

*Primary Examiner*—Bernard Helfin
*Attorney, Agent, or Firm*—Curtis, Morris & Safford

[57] ABSTRACT

Process for the preparation of 4-phenoxyphenols of the formula

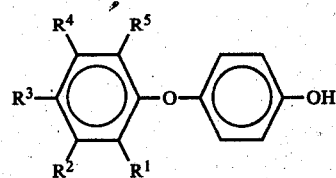

I in which $R^1$ through $R^5$ are hydrogen, halogen or alkyl, by diazotization of amines of the formula

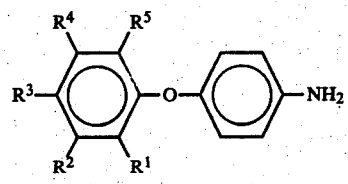

II in a hydrochloric acid medium, and boiling in aqueous sulfuric acid at 110° to 150° C.

4 Claims, No Drawings

PROCESS FOR THE PREPARATION OF 4-PHENOXYPHENOLS

Subject of the invention is a process for the preparation of 4-phenoxyphenols of the formula

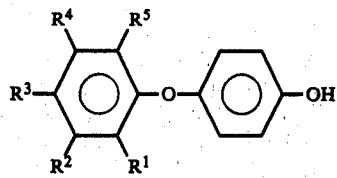

I in which $R^1$ through $R^5$, independently from each other are hydrogen, halogen or lower alkyl, by diazotization of an amine of the formula

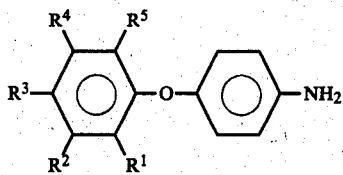

II in which $R^1$ through $R^5$ are as defined above, in an aqueous mineral acid medium, and boiling in aqueous sulfuric acid, which comprises carrying out the diazotization in hydrochloric acid and the boiling at a temperature of from 110° to 150° C.

From German Pat. No. 2,136,828 it is known that phenoxyphenols of the above kind can be prepared by diazotizing the corresponding amine in the presence of hydrochloric acid and boiling the diazonium salt. In this process, first the amine is dissolved in glacial acetic acid, then the hydrochloride is precipitated by adding hydrochloric acid and diazotization is carried out with the use of aqueous sodium nitrite solution. Subsequently borofluohydric acid is added to form the diazonium fluoborate which is then boiled in acetic anhydride. The phenol is then set free from the acetoxy compound so obtained by saponification with methanolic sodium hydroxide solution and acidification with hydrochloric acid.

The diazonium salt is separated in the form of fluoborate obviously in order to eliminate the chloride ions which, as is known, cause nuclear chlorination in a side reaction of phenol boiling (Houben-Weyl, 4th ed. 1976, vol. 6/1c, p.249), the more so the higher the halogen concentration (J. Amer. Chem.Soc. 91 (1969) 2,430).

An improved method for preparing such 4-phenoxyphenols is described in German Pat. No. 2,648,644, according to which diazotization and boiling are carried out in 60–75% sulfuric acid, preferably in the presence of catalytic amounts of alkali metal chlorides.

U.S.S.R. Pat. No. 391,128 proposes to diazotize 4,4'-diaminodiphenyl ether with a mixture of sulfuric and hydrochloric acid (3.7 g $H_2SO_4$ and 0.4 g HCl per g ether). Boiling is carried out under reflux (130° C.) in 50% sulfuric acid. In this process the concentration of chloride ions is considerably increased as compared to the process of German Pat. No. 2,648,644; consequently the yield is merely 51.5% of 4,4'-dihydroxydiphenyl ether. A prejudice existed therefore against diazotization of such amines in the presence of hydrochloric acid.

Surprisingly, it was now found that by proceeding according to the process of the invention the good yields obtained according to German Pat. No. 2,648,644 as well as the space yield can still be increased. It is furthermore surprising that despite the high chloride concentration in the boiling mixture the products are formed with a high purity degree; i.e. no significant diazonium/halogen exchange occurs.

Preferred embodiments of the invention are now described in detail as follows.

In preferred starting materials, $R^1$ through $R^5$ are hydrogen, chlorine and/or bromine. Especially preferred are starting materials where $R^1$ and $R^3$ each is hydrogen or chlorine, and $R^2$, $R^4$ and $R^5$ each is hydrogen.

Percentages indicated hereinafter are by weight unless otherwise stated.

For the diazotization the amine is introduced into about 2.1 to 5 mols of 10–36% hydrochloric acid in order to produce the hydrochloride which dissolves on heating and, when cooled with agitation, gives a suspension which can be easily stirred. Alkali metal nitrite, especially sodium nitrite, either solid or dissolved in water, is then added to this solution at 0° to 30° C.

Boiling is carried out by liberating the diazonium chloride solution from excess nitrite and adding it to a boiling mixture of an at least 60% sulfuric acid and a water-immiscible solvent for the product. Such solvents are especially aromatic hydrocarbons such as toluene and xylene. The temperature of the reaction mixture boiling under reflux is maintained nearly constant either by continuously discharging water or by adding concentrated sulfuric acid. At temperatures of up to about 150° C., yields of at least 93% of theory are obtained, the reflux temperature being adjusted by controlling sulfuric acid concentration.

Boiling is preferably carried out at 115° to 125° C. At lower temperature, formation of by-products is considerably increased, so that the yield decreases correspondingly and expensive and complicated purification becomes necessary. At a boiling temperature of from 100° to 105° C. more than 5% already of halogenation products are formed.

Because of the generally easier diazotization and the considerably increased solubility of the diazonium chlorides, higher yields and especially higher space yields are obtained as compared with the diazotization in sulfuric acid. In accordance with the invention, up to half of the amine portion remaining unreacted according to German Pat. No. 2,648,644 is converted to the phenol, although double the amine amount relative to the reaction volume is reacted.

The following examples illustrate the process of the invention.

EXAMPLE 1

220 g of 4-chloro-4'-aminodiphenyl ether are introduced into 400 ml of water and 300 g of hydrochloric acid. By heating to about 100° C., a clear solution is obtained which is cooled to 10° C. with agitation yielding an easily stirrable suspension which is diazotized with 180 g of 40% aqueous $NaNO_2$ solution. A nitrite excess is destroyed by means of amidosulfonic acid.

For boiling, 380 ml of water, 710 g of concentrated $H_2SO_4$ and 860 g of xylene are introduced into the reaction vessel and heated to 120° C. The diazonium salt solution is then introduced over a period of about 4 hours. A reflux temperature of at least 120° C. is maintained by discharging about 850 g of water via a water trap. After a further hour of stirring the gas development stops. The batch is allowed to cool with stirring, the phases are separated and the xylene solution is shaken with sodium hydroxide solution. The sodium salt solution of the phenol is acidified and the 4-chloro-4'-hydroxydiphenyl ether is separated in a molten state, washed with water and dried.

Yields: 206 g of 4-chloro-4'-hydroxydiphenyl ether (93.3% of th.)

Softening point: 83.0° C.

Purity degree: 99%±2% (Gas chromatography (GC))

Under the same reaction conditions, 4-aminodiphenyl ether was likewise converted.

Yield: 93.0% of th.

Softening point: 81.7° C.

Purity degree: 96%±2% (GC)

EXAMPLE 2

254 g of molten 2,4-dichloro-4'-aminodiphenyl ether are introduced at 80° C. into 600 ml of water and 300 g of 30% hydrochloric acid. By heating to 95° C. a clear solution is obtained which is cooled to 15° C. with agitation yielding an easily stirrable suspension, which is diazotized with 180 g of 40% aqueous $NaNO_2$ solution. A nitrite excess is destroyed by means of amidosulfonic acid.

For boiling, 190 ml of water, 480 g of concentrated $H_2SO_4$ and 1200 ml of xylene are introduced into the reaction vessel and heated to 115° C. The diazonium salt solution is then added dropwise within about 3 hours, while simulteneously 1455 g of concentrated $H_2SO_4$ are added in such a manner that a reflux temperature of at least 115° C. can be maintained. After a further hour of agitation at 115° C. the gas development stops. The batch is cooled with agitation, and the xylene solution is shaken with sodium hydroxide solution. The sodium salt solution of the phenol is acidified, the 2,4-dichloro-4'-hydroxydiphenyl ether is separated in molten state, washed with water and dried.

Yield: 243 g of 2,4-dichloro-4'-hydroxydiphenyl ether (95.3% of th.)

Softening point: 88.7° C.

Purity degree: 99%±2% (GC)

What is claimed is:

1. In a process for the preparation of a 4-phenoxyphenol of the formula

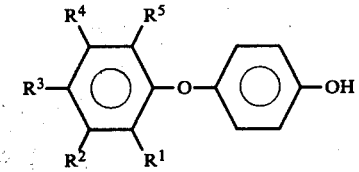

in which $R^1$ through $R^5$, independently from each other, are hydrogen, halogen or lower alkyl, by diazotization of an amine of the formula

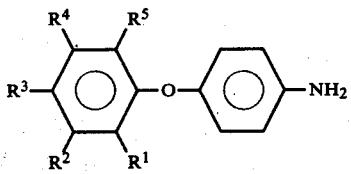

in which $R^1$ through $R^5$ are as defined above, in an aqueous mineral acid medium, and boiling, the improvement which comprises carrying out said diazotization in an acid medium consisting essentially of aqueous hydrochloric acid, and carrying out said boiling in aqueous sulfuric acid at a temperature of from 110° to 150° C. and in the presence of a water-immiscible solvent which dissolves said 4-phenoxyphenol.

2. The process as claimed in claim 1, wherein in said amine $R^1$ and $R^3$, independently from each other, are hydrogen or chlorine, and $R^2$, $R^4$ and $R^5$ are hydrogen.

3. The process as claimed in claim 1 or 2, which comprises carrying out the boiling at 115° to 125° C.

4. The process as claimed in claim 1 or 2, which comprises carrying out the diazotization in 10 to 36% hydrochloric acid.

* * * * *